United States Patent [19]

Weyer et al.

[11] 4,025,519
[45] May 24, 1977

[54] BENZENESULFONYL-UREAS

[75] Inventors: Rudi Weyer, Frankfurt am Main; Walter Aumüller, Kelkheim, Taunus; Volker Hitzel, Lorsbach, Taunus; Felix Helmut Schmidt, Mannheim, all of Germany

[73] Assignee: Hoechst Aktiengesellschaft, Frankfurt am Main, Germany

[22] Filed: Apr. 15, 1975

[21] Appl. No.: 568,268

Related U.S. Application Data

[62] Division of Ser. No. 385,323, Aug. 3, 1973, Pat. No. 3,919,245.

[30] Foreign Application Priority Data

Aug. 7, 1972 Germany .......................... 2238870

[52] U.S. Cl. ..................... 260/283 SA; 260/251 R; 260/256.4 R; 260/256.5 R; 260/287 AR; 260/287 F; 260/294.8 E; 260/294.8 H; 260/304 R; 260/305; 260/307 D; 424/251; 424/258; 424/263; 424/270; 424/272
[51] Int. Cl.² ...................................... C07D 215/38
[58] Field of Search ............. 260/283 SA, 287 AR, 260/287 F; 424/258

[56] References Cited

UNITED STATES PATENTS

| | | | |
|---|---|---|---|
| 3,655,756 | 4/1972 | Weber et al. | 260/283 SA |
| 3,705,151 | 12/1972 | Weber et al. | 260/283 SA |
| 3,709,908 | 1/1973 | Weber et al. | 260/283 SA |
| 3,751,418 | 8/1973 | Weyer et al. | 260/283 SA |
| 3,813,398 | 5/1974 | Aumüller et al. | 260/283 SA |
| 3,819,633 | 6/1974 | Ambrogi et al. | 260/283 SA |
| 3,887,561 | 6/1975 | Evanga et al. | 260/283 SA |

*Primary Examiner*—Donald G. Daus
*Assistant Examiner*—Mary C. Vaughn
*Attorney, Agent, or Firm*—Curtis, Morris & Safford

[57] ABSTRACT

Sulfonyl-ureas of the formula

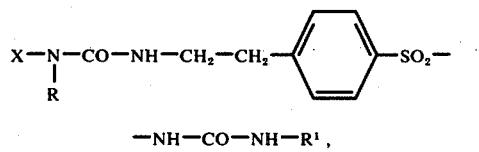

$$-NH-CO-NH-R^1,$$

wherein X represents a heteroaromatic 5- or 6-ring substituted, if desired, by one or two methyl groups and/or annellated with benzene, which ring may contain in addition to a nitrogen atom a further nitrogen, oxygen or sulfur atom and which, in vicinal position to the nitrogen atom, is linked to the rest of the molecule portion, R is alkyl having 1 to 3 carbon atoms, $R^1$ is alkyl having 3 to 6 carbon atoms, cycloalkyl, alkylcycloalkyl, cycloalkylalkyl, cycloalkenyl, alkylcycloalkenyl having each 5 to 9 carbon atoms, cyclohexenylmethyl, chlorocyclohexyl, bicycloheptenylmethyl, bicycloheptylmethyl, bicycloheptenyl, bicycloheptyl, nortricyclyl, adamantyl, benzyl, which as substance or in form of the salts thereof have hypoglycemic properties and are distinguished by a strong and continuous lowering of the blood sugar level, process for preparing them as well as pharmaceutical preparations containing the sulfonyl-ureas as an active substance.

6 Claims, No Drawings

BENZENESULFONYL-UREAS

This is a division of application Ser. No. 385,323, filed Aug. 3, 1973, and now U.S. Pat. No. 3,919,245, issued Nov. 11, 1975.

The present invention relates to sulfonyl-ureas of the formula

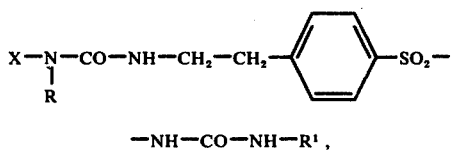

—NH—CO—NH—R$^1$, which as substance or in form of the salts thereof have hypoglycemic properties and are distinguished by a strong and continuous lowering of the blood sugar level.

In the formula X represents a heteroaromatic 5- or 6-ring substituted, if desired, by one or two methyl groups and/or annellated with benzene, which ring may contain in addition to a nitrogen atom a further nitrogen, oxygen or sulfur atom and which, in vicinal position to the nitrogen atom, is linked to the rest of the molecule portion, R is alkyl having 1 to 3 carbon atoms, R$^1$ is alkyl having 3 to 6 carbon atoms, cycloalkyl, alkylcycloalkyl, cycloalkylalkyl, cycloalkenyl, alkylcycloalkenyl having each 5 to 9 carbon atoms, cyclohexenylmethyl, chlorocyclohexyl, bicycloheptenylmethyl, bicycloheptylmethyl, bicycloheptenyl, bicycloheptyl, nortricyclyl, adamantyl, benzyl.

The invention further relates to processes for preparing these sulfonyl-ureas. They comprise a. reacting benzenesulfonyl-isocyanates, benzenesulfonylcarbamic acid esters, -thiolcarbamic acid esters, sulfonylureas, sulfonyl-semicarbazides or -semicarbazones substituted in 4-position by the group

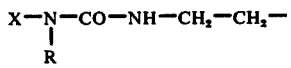

with an amine R$^1$—NH$_2$ or the salts thereof or reacting sulfonamides of the formula

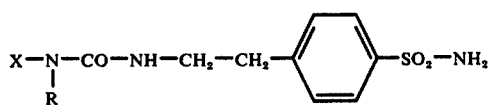

or the salts thereof with R$^1$-substituted isocyanates, carbamic acid esters, thiolcarbamic acid esters, carbamoyl halides or ureas ureas, b. splitting correspondingly substituted benzenesulfonylisourea ethers, -thiourea ethers, -parabanic acids or haloformic acid amidines, c. replacing in benzenesulfonyl-thioureas substituted by the group

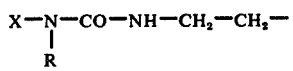

the sulfur atom by an oxygen atom, d. adding water onto the corresponding benzensulfonylcarbodiimides substituted by the group

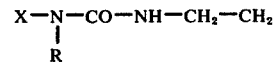

e. oxydizing corresponding benzenesulfinyl- or sulfenylureas, f. introducing into benzensulfonyl-ureas of the formula

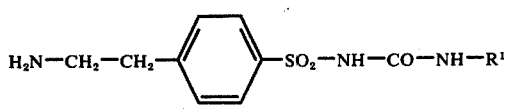

the radical

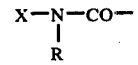

if desired, in one or more steps, g. reacting correspondingly substituted benzene-sulfonyl halides with R$^1$-substituted ureas or the alkali salts thereof, or reacting correspondingly substituted benzenesulfonic acid halides or, in the presence of acid condensation agents, correspondingly substituted sulfinic acids or the alkali salts thereof, with N-R$^1$-N'-hydroxy- ureas, and treating the reaction products, if desired, with alkaline agents for the formation of a salt.

The benzenesulfonyl-carbamic acid esters of benzenesulfonyl-thiolcarbamic acid esters mentioned may contain in the alcohol component an alkyl radical, an aryl radical or a heterocyclic radical. Since this radical is split off during the reaction, its chemical constitution has no influence on the nature of the final product and may, thus, be varied within wide limits. The same applies to the N-R$^1$-substituted carbamates or to the corresponding thiolcarbamates.

As carbamoyl halides the chlorides are preferably used.

The sulfonyl-ureas used as starting materials of the process can be unsubstituted, mono- or, especially, disubstituted at the side of the urea molecule opposite to the sulfonyl group. Since these substituents are split off in the reaction with the amines, their nature may be varied within wide limits. In addition to alkyl, acyl, aryl or heterocyclically substituted benzenesulfonyl-ureas there may also be used benzenesulfonyl-carbamoylimidazoles and similar compounds, or bis(benzenesulfonyl)-ureas which may carry on one of the nitrogen atoms one further substituent, for example, a methyl group. Those bis-(benzenesulfonyl)-ureas or N-benzenesulfonyl-N'-acyl-ureas may be treated for example with R$^1$-substituted amines and the salts obtained heated to elevated temperatures, especially to a temperature above 100° C.

Furthermore it is possible to start from R$^1$-substituted ureas or from R$^1$-substituted ureas which are mono- or, especially, di-substituted at the free nitrogen atom, and to react them with benzensulfonamides carrying in 4-position the substituent

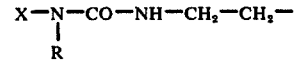

As such starting materials may be used for example N-cyclohexyl-urea, the corresponding N'-acetyl, N'-nitro, N'-cyclohexyl, N',N'-diphenyl-ureas (in which case both phenyl radicals may also be substituted or linked to each other either directly or by means of a bridge member, for example, —CH$_2$—, —NH—, —O— or —S—), N'-methyl-N'-phenyl-, N',N'-dicyclohexyl ureas as well as cyclohexyl-carbamoyl-imidazoles, -pyrazoles or -triazoles and compounds mentioned which carry, instead of the cyclohexyl group, another substituent having one of the definitions given for R$^1$.

The hydrolysis of the sulfonyl-parabanic acids, sulfonylisourea ethers, sulfonyl-isothiourea ethers or sulfonylhaloformic acid amidines mentioned as starting substances is suitably carried out in an alkaline medium. Isourea ethers may also be hydrolized successfully in an acid medium.

The replacement of the sulfur atom in the urea group of correspondingly substituted sulfonylthio-ureas by an oxygen atom can be effected in known manner, for example, with the aid of oxides or salts of heavy metals or with the use of oxidizing agents such, for example, as hydrogen peroxide, sodium peroxide, nitrous acid or permanganates.

The thioureas may also be desulfurized by treatment with phosgene or with phosphorus pentachloride. Chloroformic acid amidines or carbodiimides obtained as an intermediate stage may be converted into the sulfonyl ureas by suitable measures, for example, by saponification or addition of water.

Carbodiimides at which water is added according to process (d) may be obtained for example from correspondingly substituted thio-ureas.

The reaction conditions for carrying out the variations of the process of the invention may, in general, be modified within the wide limits and adapted to each case, for example, the reactions may be carried out with the use of solvents or without solvents, at room temperature or at an elevated temperature.

Depending on the nature of the starting substances, one or other of the variations of the process hereinbefore described may, in some cases, provide a desired, individual sulfonylurea only in a small yield or may be inappropriate for its synthesis. In such comparatively rare cases the expert will have no difficulty in synthesizing the desired product according to one of the other methods of the process described.

The hypoglycemic action of the benzenesulfonyl-urea described can be ascertained by administering them as free compounds or in the form of their sodium salts, to normally fed rabbits, in doses of 10 mg/kg of body weight and determining the blood sugar level for a prolonged period of time by the method of Hagedorn-Jensen or by means of an autoanalyser.

The following Table lists the hypoglycemic action of some compounds obtained according to the present process:

TABLE

% Lowering of the blood sugar in rabbits after administration of 10 mg/kg of the following compounds after.......hours:
N-[4-(β-N'-methyl-N'-2-pyridylureidoethyl)-benzenesulfonyl]-N'-(4-methylcyclohexyl)-urea (compound I)
N-[4-(β-N'-2-quinolyl-N'-methylureidoethyl)-benzenesulfonyl]-N'-cyclohexyl-urea (compound II)
N-[4-(β-N'-2-quinolyl-N'-methylureidoethyl)-benzenesulfonyl]-N'-cyclopentyl-urea (compound III)

| Compound | hours | | | | | |
|---|---|---|---|---|---|---|
| | 1 | 3 | 6 | 24 | 48 | 72 |
| I | 45 | 41 | 44 | 40 | 17 | 0 |
| II | 43 | 35 | 29 | 49 | 18 | 0 |

TABLE-continued

| III | 23 | 12 | 25 | 31 | 19 | 0 |
|---|---|---|---|---|---|---|

The benzenesulfonyl-ureas of the invention are preferably used for the preparation of pharmaceutical preparations suitable for oral administration for the lowering of the blood sugar level in the treatment of diabetes mellitus and may be used as such or in the form of their physiologically tolerable salts or in the presence of substances which cause such salt formation. For the formation of salts, there may be used, for example, bases, for example, alkali metal or alkaline earth metal hydroxides or alkali metal or alkaline earth metal carbonates or bicarbonates.

The pharmaceutical preparations are advantageously in the form of tablets which comprise, in addition to the compounds of the invention, pharmaceutically suitable carriers, for example, talc, starch, lactose, tragacanth and magnesium stearate.

A pharmaceutical preparation comprising the sulfonyl-ureas of the invention as the active substance, for example, a tablet or a powder with or without carriers, is advantageously brought into a suitable unit dosage form. The dose chosen should comply with the activity of the sulfonyl-urea used and with the desired effect. Advantageously, the dosage per unit amounts to from 1 to 100 mg, preferably from 5 to 20 mg, but higher or lower dosage units may also be used, which, if desired, are divided or multiplied prior to their administration.

The sulfonyl-ureas of the invention may be used either individually for the treatment of diabetes mellitus or may be combined with other oral antidiabetics. Such compounds are not only hypoglycemic sulfonyl-ureas, but also compounds having different chemical compositions such, for example, as biguanides, especially the phenylethyl-biguanide or the dimethyl-biguanide.

The following Examples illustrate some of the numerous variations of the process which may be used for the synthesis of the sulfonyl-ureas of the invention, without limiting the object of the invention.

EXAMPLE 1

N-[4-(β-N'-2-quinolyl-N--methylureidoethyl)-benzenesulfonyl]-N'-cyclohexyl-urea a. 4-(β-N'-2-quinolyl-N'-methylureidoethyl)-benzene-sulfonamide 76.5 Grams of 2-methylaminoquinoline were mixed in 600 ml of absolute benzene with 39.5 g of pyridine and, while cooling with ice and stirring, treated with 49 g of phosgene. Stirring was continued for 1 hour, the salt precipitated was suction-filtered and washed well with benzene. The filtrate was evaporated, the residue taken up in 100 ml of acetone and added dropwise, while stirring and cooling with ice, to a mixture which contained in 290 ml of water 0.36 mol of 4-(β-aminoethyl)-benzenesulfonamide and 0.72 mol of sodium acetate and was mixed with 290 ml of acetone. Stirring was continued for about 1 hour, the mixture was mixed with water, suction-filtered and recrystallized from ethanol - dimethylformamide. The reaction product obtained melted at 185°–187° C.

b. N-[4-(β-N'-2-quinolyl-N'-methylureidoethyl)benzenesulfonyl]-N'-cyclohexyl-urea 9.6 Grams of 4-(β-N'-2-quinolyl-N'-methylureidoethyl)-benzene-sulfonamide were heated in 100 ml of acetone with 5 g of ground potassium carbonate for 2 hours at the reflux condenser while stirring. 3.1 Grams of cyclohexylisocyanate were added and the mixture was refluxed for another 6 hours, while stirring. Then the acetone was evaporated, the residue was treated with water, while heating, the solution was filtered and the filtrate acidified. The precipitate was suction-filtered and recrystallized from ethanol-dimethylformamide. The N'[4-(β-N'-2-quinolyl-N'-methylureidoethyl)-benzenesulfonyl]-N'-cyclohexyl-urea obtained melted at 185°–187° C.

In analogous manner were obtained the
N-[4-(β-N'-2-quinolyl-N'-methylureidoethyl)-benzenesulfonyl]-N'-(4-methylcyclohexyl)-urea having a melting point of 180°–182° C (from ethanol-dimethylfurmamide), N-[4-(β-N'-2-quinolyl-N'-methylureidoethyl)-benzenesulfonyl]-N'-isobutyl-urea having a melting point of 165°–167° C (from ethanol)

N-[4-(β-N'-2-quinolyl-N'-methylureidoethyl)-benzenesulfonyl]-N'-(4-ethylcyclohexyl)-urea having a melting point of 169°–171° C (from ethanol)

N-[4-(β-N'-2-quinolyl-N'-methylureidoethyl)-benzenesulfonyl]-N'-cyclohex-3-enyl-urea having a melting point of 181°–183° C (from ethanol-DMF)

N-[4-(β-N'-2-quinolyl-N'-methylureidoethyl)-benzenesulfonyl]-N'-4,4-dimethylcyclohexyl-urea having a melting point of 170°–172° C (from ethanol)

In analogous manner were obtained from the 2-methylamino-4-methylquinoline by means of the 4-(β-N'-<4-methyl-2-quinolyl>-N'-methylureidoethyl)-benzenesulfonamide (melting point: 192°–194° C) the N-[4-(β-N'-<4-methyl-2-quinolyl>-N'-methylureidoethyl)-benzenesulfonyl]-N'-cyclohexyl-urea (melting point: 151°–153° C) (from ethanol-DMF)

N-[4-(β-N'-<4-methyl-2-quinolyl>-N'-methylureidoethyl)-benzenesulfonyl]-N'-(4-methylcyclohexyl)-urea (melting point: 158°–160° C) (from ethanol-DMF)

N-[4-(β-N'-<4-methyl-2-quinolyl>-N'-methylureidoethyl)-benzenesulfonyl]-N'-butyl-urea (melting point: 168°–170° C)

In analogous manner were obtained from the 2-ethylaminoquinoline (prepared by heating the 2-chloroquinoline with ethylamine solution to 200° C) by means of the 4-(β-N'-ethyl-N'-2-quinolylureidoethyl)-benzenesulfonamide (melting point 197°–199° C) the N-[4-(β-N'-ethyl-N'-2-quinolylureidoethyl)-benzenesulfonyl]-N'-cyclohexyl-urea having a melting point of 175°–177° C (from ethanol-DMF)

N-[4-(β-N'-ethyl-N'-2-quinolylureidoethyl)-benzenesulfonyl]-N'-(4-methylcyclohexyl)-urea (melting point: 161°–163° C) (from ethanol)

In analogous manner were obtained from the 2-propylaminoquinoline by means of the 4-(β-N'-2-quinolyl-N'-propylureidoethyl)-benzenesulfonamide (melting point: 189°–191° C) the N-[4-(β-N'-2-quinolyl-N'-propylureidoethyl)-benzenesulfonyl]-N'-cyclohexyl-urea (melting point: 181°–183° C) (from ethanol)

N-[4-(β-N'-2-quinolyl-N'-propylureidoethyl)-benzenesulfonyl]-N'-(4-methylcyclohexyl)-urea (melting point: 148°–150° C) (from ethanol)

N-[4-(β-N'-2-quinolyl-N'-propylureidoethyl)-benzenesulfonyl]-N'-isobutyl-urea (melting point: 146°–148° C) (from water-ethanol)

In analogous manner were obtained from the 2-methylaminopyridine by means of the 4-(β-N'-methyl-N'-2-pyridylureidoethyl)-benzenesulfonamide (melting point: 177°–178° C) the N-[4-(β-N'-methyl-N'-2-pyridylureidoethyl)-benzenesulfonyl]-N'-cyclohexyl-urea (melting point: 167°–169° C) (from ethanol-DMF)

N-[4-(β-N'-methyl-N'-2-pyridylureidoethyl)-benzenesulfonyl]-N'-(4-methylcyclohexyl)-urea (melting point: 185°–187° C) (from ethanol-DMF)

N-[4-(β-N'-methyl-N'-2-pyridylureidoethyl)-benzenesulfonyl]-N'-isobutyl-urea (melting point: 142°–144° C) (from ethanol-water)

In analogous manner were obtained from the 4,6-dimethyl-2-methylaminopyrimidine by means of the 4-(β-N'-<4,6-dimethyl-2-pyrimidinyl>-N'-methylureidomethyl)-benzenesulfonamide (melting point: 176°–178° C) the N-[4-(β-N'-<4,6-dimethyl-2-pyrimidinyl>-N'-methylureidomethyl)-benzenesulfonyl]-N'-cyclohexyl-urea (melting point: 176°–178° C) (from water-ethanol)

N-[4-(β-N'-<4,6-dimethyl-2-pyrimidinyl>-N'-methylureidoethyl)-benzenesulfonyl]-N'-(4-methylcyclohexyl)-urea (melting point: 154°–156° C) (from ethanol-water)

N-[4-(β-N'-<4,6-dimethyl-2-pyrimidinyl>-N'-methylureidoethyl)-benzenesulfonyl]-N'-isobutyl-urea (melting point: 136°–137° C) (from ethanol-water)

N-[4-(β-N'-<4,6-dimethyl-2-pyrimidinyl>-N'-methylureidoethyl)-benzenesulfonyl]-N'-(4-ethylcyclohexyl)-urea (melting point: 189°–190° C) (from ethanol-DMF)

In analogous manner were obtained from the 2-methylaminobenzthiazol by means of the 4-(β-<N'-2-benzthiazolyl-N'-methylureido>ethyl)-benzenesulfonamide (melting point: 184°–186° C) the N-[4-(β-<N'-2-benzthiazolyl-N'-methylureido>-ethyl)-benzenesulfonyl]-N'-cyclohexyl-urea (melting point: 144°–146° C) (from acetonitrile)

In analogous way were obtained from the 2-methylbenzoxazol by means of the 4-(β-<N'-2-benzoxazolyl-N'-methylureido>-ethyl)-benzenesulfonamide (melting point: 202°–204° C) the N-[4-(β-<N'-2-benzoxazolyl-N'-methylureido>-ethyl)-benzenesulfonyl]-N'-(4-methylcyclohexyl)-urea (melting point: 195°–197° C) (from ethanol)

EXAMPLE 2

N-[4-(β-N'-2-quinolyl-N'-methylureidoethyl)-benzenesulfonyl]-N'-cyclopentyl-urea 5.6 Grams of 4-(β-N'-2-quinolyl-N'-methylureidoethyl)-benzenesulfonyl-carbamic acid methyl ester (melting point 205°–206° C) prepared from 4-(β-N'-2-quinolyl-N'-methylureidoethyl)-benzenesulfonamide and chloroformic acid methyl ester) were heated to gentle boiling in 75 ml of dioxane with 1.1 g of cyclopentylamine at the descendent cooler for half an hour. Then the dioxane was evaporated under reduced pressure and the residue was recrystallized from ethanol-dimethylformamide. The N-[4-(β-N'-2-quinolyl-N'-methylureidoethyl)-benzenesulfonyl]-N'-cyclopentyl-urea obtained melted at 168°–170° C. In analogous manner were obtained the N-[4-(β-N'-2-quinolyl-N'-methylureidoethyl)-benzenesulfonyl]-N'-cycloheptyl-urea having a melting point of 167°–168° C (from ethanol-DMF)

N-[4-(β-N'-2-quinolyl-N'-methylureidoethyl)-benzenesulfonyl]-N'-cyclopentylmethyl-urea having a melting point of 157°–159° C (from ethanol)

N-[4-(β-N'-2-quinolyl-N'-methylureidoethyl)-benzenesulfonyl]-N'-(4-isopropylcyclohexyl)-urea having a melting point of 170°–172° C (from ethanol)

N-[4-(β-N'-2-quinolyl-N'-methylureidoethyl)-benzenesulfonyl]-N'-(3-methylcyclopentyl)-urea having a melting point of 164°–166° C (from ethanol)

N-[4-(β-N'-2-quinolyl-N'-methylureidoethyl)-benzenesulfonyl]-N'-n-propyl-urea having a melting point of 165°–167° C (from ethanol)

N-[4-(β-N'-2-quinolyl-N'-methylureidoethyl)-benzenesulfonyl]-N'-n-hexyl-urea having a melting point of 151°–153° C (from ethanol-water)

N-[4-(β-N'-2-quinolyl-N'-methylureidoethyl)-benzenesulfonyl]-N'-benzyl-urea having a melting point of 170°–172° C (from ethanol-DMF)

N-[4-(β-N'-2-quinolyl-N'-methylureidoethyl)-benzenesulfonyl]-N'-nortricyclyl-urea having a melting point of 162°–164° C (from ethanol-water)

N-[4-(β-N'-2-quinolyl-N'-methylureidoethyl)-benzenesulfonyl]-N'-cyclooctyl-urea having a melting point of 176°–178° C (from ethanol-water)

N-[4-(β-N'-2-quinolyl-N'-methylureidoethyl)-benzenesulfonyl]-N'-cyclohexylmethyl-urea having a melting point of 163°–165° C (from ethanol-water)

In analogous manner were obtained by means of the 4-(β-N'-ethyl-N'-2-quinolylureidoethyl)-benzenesulfonylcarbamic acid methyl ester (melting point 155°–177° C) the N-[4-(β-N'-ethyl-N'-2-quinolylureidoethyl)-benzenesulfonyl]-N'-(bicyclo[2.2.1]hept-2-yl)-urea having a melting point of 168°–170° C (from ethanol-water)

N-[4-(β-N'-2-quinolyl-N'-ethylureidoethyl)-benzenesulfonyl]N'-(bicyclo[2.2.1]hept-5-en-2-yl)-urea having a melting point of 164°–166° C (from water-ethanol)

In analogous manner was obtained from the 4-(β-N'-methyl-N'-2-pyridyl-ureidoethyl)-benzenesulfonylcarbamic acid methyl ester having a melting point of 164°–165° C the N-[4-(β-N'-methyl-N'-2-pyridyl-ureidoethyl)-benzenesulfonyl]-N'-adamantyl-urea having a melting point of 127°–128° C (from ethanol-water)

EXAMPLE 3

N-[4-(β-<N'-methyl-N'-2-pyridyl-ureido>-ethyl)-benzenesulfonyl]-N'-cyclohexyl-urea 5 Grams N-[4-(β-<N'-methyl-N'-2-pyridyl-ureido>-ethyl)-benzenesulfonyl]-N'-cyclohexyl-thio-urea (prepared by reaction of 4-(β-<N'-methyl-N'-2-pyridyl-ureido>-ethyl)-benzenesulfonamide and cyclohexylisothiocyanate in an acetonic solution in the presence of potassium carbonate, melting point 143°–145° C from methanol) were dissolved in 50 ml of 1N sodium hydroxide solution. 5 Milliliters of 30% $H_2O_2$ were added and the mixture was heated for 15 minutes on the steam bath. After cooling the solution was acidified. The precipitate was suction-filtered and recrystallized from ethanol/dimethylformamide. The N'-[4-(β-<N'-methyl-N'-2-pyridyl-ureido>-ethyl)-benzenesulfonyl]-N'-cyclohexyl-urea obtained melted at 167°–169° C.

EXAMPLE 4

N-[4-(β-<N'-methyl-N'-2-pyridyl-ureido>-ethyl)-benzenesulfonyl]-N'-cyclohexyl-urea 2.38 Grams of N-[4-(β-<N'-methyl-N'-2-pyridyl-ureido>-ethyl)-benzenesulfonyl]-N'-cyclohexyl-thiourea were dissolved in 100 ml of methanol. 3 Grams of mercury oxide and a spatula tip covered with potassium carbonate were added, and the mixture was heated to about 40° C for 6 hours, while heating. The mercury sulfide being formed was suction-filtered and the solvent was evaporated from the filtrate under reduced pressure. The N-[4-(β-<N'-methyl-N'-2-pyridyl-ureido>-ethyl)-benzenesulfonyl]-N'-cyclohexyl-isourea methyl ether was obtained in a very good yield as a viscous resin which crystallized when triturated. The melting point was 117°–118° C after recrystallization from isopropanol.

Concentrated hydrochloric acid has been poured on a sample of the N-[4-(β-<N'-methyl-N'-2-pyridyl-ureido>-ethyl)-benzenesulfonyl]-N'-cyclohexylisoureamethyl ether thus obtained. The whole was heated on the steam bath, diluted with water, made alkaline with diluted ammonia and filtered. By acidifying with acetic acid the N-[4-(β-<N'-methyl-N'-2-pyridyl-ureido>-ethyl)-benzenesulfonyl]-N'-cyclohexyl-urea precipitated. After recrystallization from dimethylformamide/ethanol the substance melted at 167°–169° C.

What is claimed is:

1. A benzenesulfonyl-urea of the formula

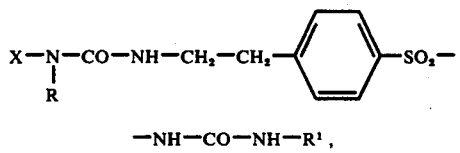

—NH—CO—NH—R¹, in which X represents a quinolyl or a substituted quinolyl having one or two methyl groups which, in vicinal position to the nitrogen atom, is linked to the rest of the molecule, R is alkyl of 1 to 3 carbon atoms and R¹ is alkyl of 3 to 6 carbon atoms, cycloalkyl, alkylcycloalkyl, cycloalkylalkyl, cycloalkenyl or alkylcycloalkenyl each having to 9 carbon atoms, cyclohexenylmethyl, chlorocyclohexyl, bicycloheptenylmethyl, bicycloheptylmethyl, bicycloheptenyl, bicycloheptyl, nortricyclyl, adamantyl, benzyl, or a physiologically tolerable salt thereof.

2. The compound as defined in claim 1 wherein X is quinolyl, R is methyl, and R¹ is cyclohexyl.

3. The compound as defined in claim 1 wherein X is quinolyl, R is methyl, and R¹ is cyclopentyl.

4. The compound as defined in claim 1 wherein X is quinolyl, R is methyl, and R¹ is 4-methylcyclohexyl.

5. A pharmaceutical preparation for oral administration and lowering the blood sugar level in the treatment of diabetes mellitus, which comprises, in a unit dose of 1 to 100 mg, a benzenesulfonyl-urea as claimed in claim 1 or a physiologically tolerable salt thereof and an inert carrier therefor.

6. A process for lowering the blood sugar level in the treatment of diabetes mellitus which comprises administering orally to the patient an effective amount of a benzenesulfonyl-urea as claimed in claim 1 or a physiologically tolerable salt thereof.

* * * * *